(12) United States Patent
Jaynes et al.

(10) Patent No.: US 7,288,622 B1
(45) Date of Patent: Oct. 30, 2007

(54) COMPOSITION FOR TREATMENT OF BURNS AND WOUNDS

(75) Inventors: Jesse Jaynes, Auburn, AL (US); Ramakrishnareddy Isanaka, Warren, NJ (US)

(73) Assignee: Issar Pharmaceuticals Pvt Ltd, Hyderabad (IN)

( * ) Notice: Subject to any disclaimer, the term of this patent is extended or adjusted under 35 U.S.C. 154(b) by 0 days.

(21) Appl. No.: 11/523,477

(22) Filed: Sep. 19, 2006

(51) Int. Cl.
*A61P 17/02* (2006.01)

(52) U.S. Cl. .................. 530/300; 530/310; 424/78.06; 424/78.05; 424/78.07; 514/2

(58) Field of Classification Search ...................... None
See application file for complete search history.

(56) References Cited

U.S. PATENT DOCUMENTS

| | | | |
|---|---|---|---|
| 4,434,179 A * | 2/1984 | Kobayashi et al. ......... 514/533 |
| 5,407,670 A | 4/1995 | Shinault | |
| 5,561,107 A | 10/1996 | Jaynes et al. | |
| 5,955,573 A | 9/1999 | Garvarino et al. | |
| 5,997,876 A | 12/1999 | Shikhashvili | |
| 2004/0037897 A1 * | 2/2004 | Benjamin et al. ............ 424/718 |
| 2004/0229808 A1 * | 11/2004 | Owen .......................... 514/13 |
| 2005/0036950 A1 | 2/2005 | Jones et al. | |

OTHER PUBLICATIONS

Ballweber LM, Jaynes JE, Stamm WE, Lampe MF, In Vitro Microbicidal Activities of Cecropin Peptides D2A21 and D4E1 and Gel Formulations Containing 0.1 to 2% D2A21 against Chlamydia trachomatis, ANtimicrobial Agents and Chemotherapy, 2002, 46(1): 34-41.*

Burns in the Merck manual.*

* cited by examiner

*Primary Examiner*—Anish Gupta
*Assistant Examiner*—Julie Ha
(74) *Attorney, Agent, or Firm*—Dodds and Associates; Susanne Somersalo; John Dodds

(57) ABSTRACT

A composition is provided to heal burns, wounds and other skin traumas of mammals. The composition is useful to treat sepsis and to improve skin formation as well. The composition comprises an antimicrobial peptide having amino acid sequence FAKKFAKKFKKFAKKFAKFAFAF.

18 Claims, No Drawings

SEQUENCE LISTING

```
<160> NUMBER OF SEQ ID NOS: 1

<210> SEQ ID NO 1
<211> LENGTH: 23
<212> TYPE: PRT
<213> ORGANISM: artificial
<220> FEATURE:
<223> OTHER INFORMATION: chemically synthetized

<400> SEQUENCE: 1

Phe Ala Lys Lys Phe Ala Lys Lys Phe Lys Lys Phe Ala Lys Lys Phe
1               5                   10                  15

Ala Lys Phe Ala Phe Ala Phe
            20
```

COMPOSITION FOR TREATMENT OF BURNS AND WOUNDS

SEQUENCE DATA

This application contains sequence data provided on a computer readable diskette and as a paper version. The paper version of the sequence data is identical to the data provided on the diskette.

TECHNICAL FIELD

This invention relates generally to the field of biochemistry and medicine. More particularly, the present invention relates to compositions useful for treatment of burns and wounds, as well as for prevention of burns and wound sepsis and for skin regeneration.

BACKGROUND ART

Topical wound and burn ointments, creams and sprays are commonly used all over the world. The compositions usually contain wound cleaners, wound healing agents, antimicrobial compounds and so on. Compounds such a hydrocortisone, zinc oxide and antibiotics are common ingredients of such ointments and sprays. Over the counter topical antibiotics, such as neosporin and bacitracin are commonly used to treat skin infections and promote wound healing. Known are also various ointments that contain various natural plant extracts, such as calendula or aloe vera extract. U.S. Pat. No. 5,997,976 for example discloses a burn and wound ointment containing such natural plant extracts.

Bactericidal ointments for the treatment of wounds are well known. Such ointments typically contain an antibiotic or an anti-bacterial agent in an inert vehicle or carrier, such as a paraffin base ointment or an oil-in-water emulsion. U.S. Pat. No. 5,407,670 for example discloses a topical ointment including a mixture of antibiotics to be used for healing epidermal trauma. Also other formulations, such as sprays or foams are known in the art: U.S. patent application Ser. No. 10/639,991 discloses a wound spray for example.

A disadvantage of antibiotic treatment is that bacteria often develop tolerance and resistance to the medication over time, and thus become difficult to eradicate. A prime example is *Staphylococcus aureus*, which has become resistant to many commonly used antibiotics. As a result antibiotic resistant *Staphylococcus*-strains are serious problem in hospitals all over the world. Therefore, there is a need for alternative compositions to effectuate healing of wounds and burns and to prevent invasive sepsis.

Recently, novel peptides have been disclosed for antimicrobial purposes. U.S. Pat. No. 5,561,107 discloses a number of amphipatic peptides to treat wounds by stimulating fibroblast and keratinocyte growth in vivo. U.S. Pat. No. 5,955,573 discloses sequences of various lytic peptides and lytic peptide fusion expression vectors.

There is however, a variety of art-recognized problems associated with formulating peptides into pharmaceutically acceptable compositions. It is well known that amphipatic peptides for example are extremely sensitive to their local environment and that it is a great challenge to maintain the activity of peptides in pharmaceutical compositions. Protein aggregation is known to be a source of instability of the peptides and this problem may arise during manufacturing process. Similarly such instability problems may arise during storage. In addition to lowered stability aggregation may result in loss of efficacy, altered pharmacokinetics, as well as unwanted immunogenicity Accordingly, there is a need to topical formulations comprising active antimicrobial peptides. There is also a clear need for topical antibacterial agent having a large spectrum of activity against bacteria and fungi.

Pursuant to the present invention, healing of burns and wounds as well as prevention invasive bacterial/fungal sepsis in mammals is promoted through the use of a specific composition comprising an effective amount of the antimicrobial peptide disclosed herein.

Other objects and advantages of the present invention will be more fully apparent from the disclosure and claims below.

DISCLOSURE OF INVENTION

This present invention describes use of a synthetic peptide in treatment of burns and wounds, as well as of burns and wound sepsis and a formulation for topical treatment of such epidermal trauma.

This invention pertains to antibacterial wound and burn healing composition which comprises an antibacterial peptide as the active ingredient.

The active ingredient of the ointment is a fully synthetic peptide consisting of 23 amino acids and having amino acid sequence FAKKFAKKFKKFAKKFAKFAFAF (SEQ ID NO: 1).

The peptide according to this disclosure is non-toxic and it is not characterized by allergic or local-irritation actions. By bacteriological experiments the peptide has been proven to have high antibacterial activity over various bacterial groups. The examples below show activity against gram-negative as well as gram-positive bacteria.

The mechanism of action of the peptide appears to be pore formation in the membranes of microorganisms. The peptide binds to the membranes, aggregates within the membrane and ultimately forms pores in the membrane, thereby killing the microbe cells. Due to this mechanism of action the peptide has activity also on fungal cells. Moreover the peptide has cytotoxic activity on cancer cells.

The preferred embodiment according to the present invention is a topical formulation containing less than 2% per weight of the peptide according to SEQ ID NO:1. The invention is described in more details in the examples below.

EXAMPLE 1

Characterization of the Active Peptide Ingredient

The active ingredient of the ointment is a fully synthetic peptide consisting of 23 amino acids and having an amino acid sequence FAKKFAKKFKKFAKKFAKFAFAF (SEQ ID NO:1).

The counter ion associated with cationic side chains in the peptide is acetate ion. The peptide was synthesized by solid-phase peptide synthesis.

The molecular weight of the peptide is 2776 and 3388 with counter ions. The peptide is water-soluble and forms an alpha helical secondary protein structure. Solubility of the peptide in saline is 31.58 μmoles/ml and solubility in 10% DMSO in saline is 32.25 μmoles/ml. A four-week stability study of the peptide in saline at −20° C.; 5° C. and 25° C. gave recoveries for the peptide within 95% and 105% of the initial values.

The peptide is extremely sensitive to its local environment. Surprisingly, dimerization of the peptide yields peptides that possess clearly higher anti-bacterial activity than the monomer. It seems that in order to maintain its activity the peptide has to aggregate to a certain extent but too much of aggregation is detrimental to its activity also. Therefore, the composition of the formulation is of extreme importance to achieve a treatment with maximum efficacy.

EXAMPLE 2

Antibacterial Activity of the Peptide in Tris NaCl-Buffer pH 7.2 Tested with *Staphyloccus aureus* Bacteria The antibacterial activity of the peptide was tested against *Staphylococcus aureus* MTCC96. *Staphylococcus aureus* exemplifies the group of gram-positive bacteria. The actively growing bacterial slant culture was suspended in Tris NaCl buffer with pH 7.2 and washed thrice to prepare the inoculum. Test cultures for inoculum were prepared to get the cell density of about 0.5 O.D in Tris NaCl buffer and 0.5 ml culture suspension was inoculated in each tube containing 5 ml of test compound at different concentration. The culture was exposed to test compound at 37° C. for 0, 2, 4, and 24 hours, respectively. Controls were run without test compound but with only microbial culture inoculated into buffer tubes. Viable count of bacterial cultures was recorded at each time interval by dilution plate method to study the inhibitor effect of the test compound.

Table 1 shows the efficiency of the peptide to kill *Staphylococcus aureus*-bacteria. The peptide was capable of killing the bacteria totally within an exposure of one hour. Two different concentrations of the peptide were used and the result was the same with each.

The same experiment was conducted at pH 8.4 and the exposure time needed to kill 100% of *Staphylococcus aureus*-bacteria was then 4 hours.

TABLE 1

Antibacterial activity of the peptide measured killing % of *Staphylococcus aureus* at pH 7.2. Two different concentrations of the peptide were tested.

| Time of exposure (hours) | Concentration tested (μg/ml) | % killed |
| --- | --- | --- |
| 1 | 4.3 | 100 |
| 2 | 4.3 | 100 |
| 4 | 4.3 | 100 |
| 1 | 21.5 | 100 |
| 2 | 21.5 | 100 |
| 4 | 21.5 | 100 |

EXAMPLE 3

Antibacterial Activity of the Peptide in Tris NaCl-Buffer pH 8.4 Tested with *Pseudomonas aeruginosa* Bacteria The antibacterial activity of the peptide was tested against *Pseudomonas aeruginosa* MTCC 741. *Pseudomonas aeruginosa* exemplifies the group of gram negative bacteria. The actively growing bacterial slant culture was suspended in Tris NaCl buffer with pH 8.4 and washed thrice to prepare the inoculum. Test cultures for inoculum were prepared to get the cell density of about 0.5 O.D in Tris NaCl buffer and 0.5 ml culture suspension was inoculated in each tube containing 5 ml of test compound at different concentration. The culture was exposed to test compound at 37° C. for 0, 2, 4, and 24 hours, respectively. Controls were run without test compound but with only microbial culture inoculated into buffer tubes. Viable count of bacterial cultures was recorded at each time interval by dilution plate method to study the inhibitor effect of the test compound.

Table 2 shows the efficiency of the peptide to kill *Pseudomonas aeruginosa*-bacteria. The peptide was capable of killing the bacteria totally within one hour exposure. Two different concentrations of the peptide were used and the result was the same with each.

The same experiment was conducted at pH 7.24 and the exposure time needed to kill 100% of *Pseudomonas aeruginosa bacteria was then* 4 hours.

TABLE 2

Antibacterial activity of the peptide measured killing % of *Pseudomonas aeruginosa* at pH 8.4. Two different concentrations of the peptide were tested.

| Time of exposure (hours) | Concentration tested (μg/ml) | % killed |
| --- | --- | --- |
| 1 | 4.3 | 100 |
| 2 | 4.3 | 100 |
| 4 | 4.3 | 100 |
| 1 | 21.5 | 100 |
| 2 | 21.5 | 100 |
| 4 | 21.5 | 100 |

EXAMPLE 4

Acute Toxicity Test of the Peptide

The safety of the peptide was tested with mice and rats at age of 4 to 6 weeks. The tests were conducted with five female mice and rats and five male mice and rats. The dose of the peptide injected intraperitoneal was 8.95 mg/kg for rats and 12.53 mg/kg for mice. The acute toxicity test was conducted at $3^{rd}$, $6^{th}$, $12^{th}$ and $24^{th}$ hour after exposure to the peptide. No lethality was found at the points of inspection. The animals were active still on $14^{th}$ day. Thus the peptide does not show any acute lethality when administered once.

EXAMPLE 5

Composition of an Ointment

The peptide having amino acid sequence according to SEQ ID NO: 1 can be used as an active ingredient to improve healing of wounds and burns, to prevent burn and wound sepsis and to improve skin regeneration. The composition may also be used for treating fungal infections as well as other skin conditions such as acne, where bacterial or fungal infection plays a role. The peptide can be applied on human skin for example in form of a cream or gel. Alternatively the composition could also be an emulsion, spray or lotion or any other pharmaceutically acceptable formulation.

The compositions may contain other biologically active agents. The compositions may contain pharmaceutically acceptable carriers. A preferred composition of an ointment is provided in Table 3.

TABLE 3

A preferred composition of an antimicrobial ointment. pH of the composition is preferably between 6 and 7.

| Ingredient | Quantity in grams |
| --- | --- |
| Soft paraffin wax | 9-11 |
| Cetyl alcohol | 1-3 |
| Ceto Steryl alcohol | 1-3 |
| Sorbitan mono oleate | 2-4 |
| Light liquid paraffin | 2-4 |
| Propylene glycol | 5-7 |
| Cetomacrogol 1000 | 1-3 |
| Purified water | 73-75 |
| Peptide having amino acid sequence according to SEQ ID NO:1 | <2% by weight |
| Methyl paraben | <1% by weight when combined |
| Propyl paraben | |
| Disodium EDTA | |
| Citric acid | |

Table 3 provides guidelines to prepare the ointment. The amount of the peptide of SEQ ID NO: 1 is less than 2% (by weight) of the total composition.

EXAMPLE 5

Antimicrobial Effect of the Ointment on Human Skin

One application of ointment comprising the peptide according to SEQ ID NO: 1 was provided on wounds of human skin. The bacteria count was measured on the wound after various time periods after the ointment was applied. The ointment prevented growth of bacteria on the wound within two to four hours. After this the wound began to heal very fast. A single application of the ointment was enough to improve healing of the wound and regeneration of the skin thereafter.

While the compositions and methods of this invention have been described in terms of preferred embodiments, it will be apparent to those of skill in the art that variations may be applied to the compositions described herein without departing from the concept, spirit and scope of the invention.

mals, wherein the composition is a mixture of peptide according to SEQ ID NO: 1, soft paraffin wax, cetyl alcohol, ceto steryl alcohol, sorbitan mono oleate, light liquid paraffin, propylene glycol, cetomacrogol 1000, purified water, methyl paraben, propyl paraben, disodium EDTA and citric acid.

2. The composition of claim 1, wherein the mixture is essentially a ratio of 9-11 g of soft paraffin wax, 1-3 g of cetyl alcohol, 1-3 g of ceto steryl alcohol, 2-4 g sorbitan mono oleate, 2-4 g of light liquid paraffin, 5-7 g of propylene glycol, 1-3 g of cetomacrogol 1000, 73-75 g of purified water, less than 1 weight-% of combination of methyl paraben, propyl paraben, disodium EDTA and citric acid; and less than 2 weight-% of peptide according to SEQ ID NO: 1.

3. The composition of claim 2, to prevent growth of bacteria on a wound or a burn.

4. The composition of claim 3, wherein the bacteria is gram positive bacteria.

5. The composition of claim 4, wherein the bacteria is *Staphylococcus aureus*.

6. The composition of claim 3, wherein the bacteria is gram negative bacteria.

7. The composition of claim 6, wherein the bacteria is *Pseudomonas aeruginosa*.

8. The composition of claim 1, wherein the composition is an ointment.

9. A method for treatment of burns and wounds and for prevention of burns sepsis and wounds sepsis in mammals by administering composition of claim 1 on skin.

10. The method of claim 9, wherein the composition is a mixture of peptide according to SEQ ID NO: 1, soft paraffin wax, cetyl alcohol, ceto steryl alcohol, sorbitan mono oleate, light liquid paraffin, propylene glycol, cetomacrogol 1000, purified water, methyl paraben, propyl paraben, disodium EDTA and citric acid.

11. The method of claim 10, where in the mixture is essentially a ratio of 9-11 g of soft paraffin wax, 1-3 g of cetyl alcohol, 1-3 g of ceto steryl alcohol, 2-4 g sorbitan mono oleate, 2-4 g of light liquid paraffin, 5-7 g of propylene glycol, 1-3 g of cetomacrogol 1000, 73-75 g of purified water, less than 1 weight-% of combination of methyl paraben, propyl paraben, disodium EDTA and citric acid; and less than 2 weight-% of peptide according to SEQ ID NO: 1.

What is claimed is:

1. A composition for treatment of burns and wounds and for prevention of burns sepsis and wounds sepsis in mam-

12. The method according to claim 9, wherein the composition is administered to skin once a day.

13. The method according to claim 9, wherein the trauma is a wound or a burn.

14. The method according to claim 9, wherein the skin trauma includes bacterial or fungal infection.

15. The method according to claim 14, wherein the infection is caused by gram negative bacteria.

16. The method according to claim 15, wherein the bacteria is *Pseudomonas aeruginosa*.

17. The method according to claim 14, wherein the infection is caused by gram positive bacteria.

18. The method according to claim 17, wherein the infection is caused by *Staphylococcus aureus*.

* * * * *